United States Patent

Mano et al.

Patent Number: 5,900,144
Date of Patent: May 4, 1999

[54] SEPARATING AGENT COMPRISING BONDED CONALBUMIN

[75] Inventors: Nariyasu Mano; Yoshiya Oda, both of Ibaraki; Toshinobu Miwa, Aichi; Naoki Asakawa, Ibaraki; Yutaka Yoshida, Saitama; Tadashi Sato, Chiba, all of Japan

[73] Assignee: Eisai Co., Ltd., Tokyo, Japan

[21] Appl. No.: 08/070,434

[22] PCT Filed: Oct. 9, 1992

[86] PCT No.: PCT/JP92/01320

§ 371 Date: Jun. 2, 1993

§ 102(e) Date: Jun. 2, 1993

[87] PCT Pub. No.: WO93/07104

PCT Pub. Date: Oct. 9, 1992

[30] Foreign Application Priority Data

Oct. 9, 1991 [JP] Japan .................................. 3-289517

[51] Int. Cl.[6] .................................................. B01D 15/08
[52] U.S. Cl. .................................. 210/198.2; 210/502.1; 210/635; 210/656; 502/403
[58] Field of Search ..................... 210/635, 656, 210/198.2, 502.1; 502/403; 530/413, 417

[56] References Cited

U.S. PATENT DOCUMENTS

| | | | |
|---|---|---|---|
| 4,061,591 | 12/1977 | Oliver | 502/403 |
| 4,525,465 | 6/1985 | Someno | 502/403 |
| 4,532,232 | 7/1985 | Larsson | 502/403 |
| 4,544,485 | 10/1985 | Pinkerton | 502/403 |
| 4,681,870 | 7/1987 | Balint | 502/403 |
| 4,980,065 | 12/1990 | Hsu | 210/632 |
| 5,030,354 | 7/1991 | Miwa | 502/403 |
| 5,045,190 | 9/1991 | Carbonell | 502/403 |
| 5,240,602 | 8/1993 | Hammen | 502/403 |

FOREIGN PATENT DOCUMENTS

| | | | |
|---|---|---|---|
| 240 013 | 4/1987 | European Pat. Off. | 210/198.2 |
| 60-41619 | 3/1985 | Japan | 210/198.2 |
| 63-307829 | 12/1988 | Japan | 210/198.2 |
| 643129 | 1/1989 | Japan | 502/403 |
| 3251544 | 11/1991 | Japan | 210/198.2 |
| 1578138 | 7/1990 | U.S.S.R. | 502/403 |

OTHER PUBLICATIONS

Mikes' Laboratory Handbook of Chromatographic and Allied Methods, John Wiley & Sons, New York, 1979, pp. 402 and 403.

Hand Journal of Chromatography, vol. 603, 1992, Amsterdam, pp. 105–109.

*Primary Examiner*—Ernest G. Therkorn
*Attorney, Agent, or Firm*—Flynn, Thiel, Boutell & Tanis, P.C.

[57] ABSTRACT

Disclosed is an optical isomer separating agent composed of a stationary phase having a support and a chemically modified conalbumin. The separating agent may be used in a high-performance liquid chromatography column.

1 Claim, 2 Drawing Sheets

SEPARATING AGENT COMPRISING BONDED CONALBUMIN

FIELD OF THE ART

The present invention relates to an optical isomer separating agent which comprises a support and conalbumin bonded thereto and to a high-performance liquid chromatographic column packed with the separating agent.

BACKGROUND ART

It is known that only one of the optical isomers constituting a racemic modification has a physiological activity in the natural world. It has recently been found in the field of drugs that only one of the optical isomers constituting a racemic modification has a remarkable pharmacological effect or a low toxicity in some cases, for which the development of a drug with an isolated optical isomer has risen in importance.

Only a few methods for the separation of optical isomers can be practically conducted on an industrial scale, though many methods therefor have been known hitheroto. Therefore, a method which can separate optical isomers easily and at a low cost has been sought. In recent years, with the progress in high-performance liquid chromatography, methods for separating optical isomers have become known generally and separatory columns having various performances have also been reported.

However, there are only a few columns usable for the separation of optical isomers while it is known that very many compounds have optical isomers. In addition, not all optical isomers can always be efficiently separated, and therefore the development of a new separatory column has been expected.

DISCLOSURE OF THE INVENTION

The present inventors have extensively studied to develop an optical isomer separating agent having a new separating ability. As a result, they have found that the above object can be attained by taking the following constitution. The present invention has been accomplished on the basis of this finding.

Namely, the present invention relates to an optical isomer separating agent characterized by being composed of a stationary phase comprising a support and conalbumin or chemically modified conalbumin bonded to the support. Further, the present invention also relates to a high-performance liquid chromatographic column packed with an optical isomer separating agent characterized by being composed of a stationary phase comprising a support and conalbumin or chemically modified conalbumin bonded to the support.

According to the present invention, optical isomers which could not be separated or could only be insufficiently separated according to the prior art can be efficiently separated. Accordingly, an object of the present invention is to provide a new optical isomer separating agent which has a new optical isomer separating ability and a high-performance liquid chromatographic column packed with this new separating agent.

The support in the present invention refers to a fine support to which conalbumin can be chemically bonded, and examples thereof include silica gel, glass, cellulose, synthetic polymers and aminopropyl silica gel.

Conalbumin is a protein falling under the category of albumins and its molecular weight is 70,000 (or 87,000 according to some other reports). The pH of the isoelectric point thereof is 5.8. It exists in egg white and accounts for 13.8% of the proteins constituting the egg white.

The conalbumin used may be a commercially available one. Alternatively, the conalbumin may be prepared from egg white by a known process (Kagaku Daijiten (Encyclopaedia Chimica), Vol. 3, p.744 (1977)).

Conalbumin can be bonded to a support by a conventional process for the preparation of a stationary phase. For example, when aminopropyl silica gel is used as the support, the bonding of the conalbumin can be conducted by using N,N-disuccinimidyl carbonate as a crosslinking agent. Further, when silica gel is used as the support, the bonding of the conalbumin can be conducted by using 3-glycidoxypropyltrimethoxysilane as a crosslinking agent.

The chemically modified conalbumin in the present invention refers to conalbumin which is partially chemically converted by cross-linkage with glutaraldehyde, conversion into diol, acylation or modification with glutaraldehyde followed by reduction. Methods for chemical modification are as follows: for example, the cross-linkage of conalbumin with glutaraldehyde is conducted by adding conalbumin and glutaraldehyde to a phosphate buffer having a pH of 6.8 and stirring the obtained mixture at 30° C. for 15 hours, by which conalbumin cross-linked with glutaraldehyde is obtained. The conalbumin cross-linked with glutaraldehyde is further treated with sodium borohydride in a phosphate buffer having a pH of 6.8 at 4° C. for 12 hours under stirring to give a reduced-form conalbumin. Separately, N,N-disuccinimidyl carbonate is dissolved in acetonitrile, followed by the addition thereto of a sodium hydrogencarbonate buffer and aminopropyl silica gel to effect a reaction. After the organic solvent was washed off, the reaction product is reacted with the above chemically modified conalbumin in a sodium hydrogencarbonate buffer to give a support containing the chemically modified conalbumin bonded thereto.

Alternatively, a support containing a chemically modified conalbumin bonded thereto can also be prepared by chemically modifying a support containing conalbumin bonded thereto.

The optical isomer in the present invention refers to a chiral compound having an asymmetric carbon atom in its molecule, which includes many compounds. Examples of such a chiral compound which is used in the field of drugs include clorprenaline, ascorbic acid, ampicillin, tocopherol, epinephrine, ephedrine, quinine, phenylephrine, propranolol, methamphetamine, scopolamine, methyldopa, azelastine and verapamil.

The optical isomer separating agent according to the present invention is generally used by packing the agent into a column and attaching the resulting column to a high-performance liquid chromatograph. Accordingly, the separation of optical isomers may be conducted by conventional high-performance liquid chromatographic processes under analytical conditions including the composition of the mobile phase being suitably selected depending upon the properties of the objective substance.

BEST MODE TO PRACTICE THE INVENTION

The present invention will be described in more detail by referring to the following Examples, though the present invention is not limited to them.

EXAMPLE 1

3 g of aminopropyl silica gel and 2 g of N,N-disuccinimidyl carbonate were added to 100 ml of a 0.1M sodium hydrogencarbonate buffer (pH 6.8). The obtained mixture was stirred overnight and poured on a glass filter. The filter cake was washed with water and a suspension of activated aminopropyl silica gel was prepared. A solution of 2 g of conalbumin in 30 ml of a 0.1M sodium hydrogencarbonate buffer (pH 6.8) was separately prepared and added to the above suspension to give a separating agent according to the present invention.

EXAMPLE 2

The separating agent prepared in Example 1 was packed into a steel column to give a separatory column for optical isomers.

EXAMPLE 3

10 g of silica gel was dried at 140° C. for 24 hours, cooled and suspended in 140 ml of toluene, followed by the addition thereto of 15 ml of 3-glycidoxypropyltrimethoxysiline. The obtained mixture was refluxed with heating. After 5 hours, low-boiling substances were distilled away from the top and the resulting mixture was poured on a glass filter. The filter cake was washed with toluene, tetrahydrofuran and methanol successively and dried at 60° C. for 2 hours to give an epoxy-activated silica gel. 5 g of this activated silica gel was suspended in 50 ml of a borate buffer having a pH of 8.5, followed by the addition thereto of 500 mg of conalbumin. The obtained mixture was reacted at room temperature for 24 hours and poured on a glass filter. The filter cake was washed with water to give a separating agent according to the present invention.

EXAMPLE 4

The separating agent prepared in Example 3 was packed into a column to give a separatory column for optical isomers.

EXAMPLE 5

2 g of the support prepared in Example 1 and 0.1 g of glutaraldehyde were added to 30 ml of a 0.06M phosphate buffer (pH 6.8). The obtained mixture was stirred at 30° C. for 15 hours to form a support containing, bonded thereto, conalbumin (unreduced form) cross-linked with glutaraldehyde. Further, 0.2 g of sodium borohydride was added to the above reaction mixture, and the resulting mixture was stirred at 40° C. for 12 hours to give a support containing, bonded thereto, conalbumin (reduced form) reduced and cross-linked with glutaraldehyde.

EXAMPLE 6

The support prepared in Example 5 was packed into a column to give a separatory column for optical isomers.

Effect

The effect of the present invention will be described by referring to the following Experimental Examples.

EXPERIMENTAL EXAMPLE 1

The separation of azelastine was conducted by the use of the separatory column for optical isomers prepared in Example 2.

Conditions of high-performance liquid chromatography mobile phase: 50 mM phosphate buffer (pH 5.0) containing 8% of ethanol flow rate: 1.0 ml/min detection: 230 nm The result is shown in FIG. 1.

The peak at a retention time of 19 minutes is assignable to the d-isomer and that at a retention time of 25 minutes to the l-isomer. As apparent from the FIG. 1, the optical isomers of azelastine were separated by the use of the separating agent according to the present invention.

COMPARATIVE EXAMPLE 1

The separation of the optical isomers of azelastine was conducted by the use of a commercially available ovomucoid column (trade name: ULTRON ES-OVM) using ovomucoid, which is a glycoprotein. FIGS. 2 and 3 show the chromatograms obtained by using 2% and 1% tetrahydrofuran/20 mM phosphate buffer (pH 4.8) as the mobile phase, respectively.

As apparent from FIGS. 2 and 3, the optical isomers of azelastine could not be separated. By using methanol or acetonitrile as the mobile phase, the optical isomers of azelastine could not be separated as well.

EXPERIMENTAL EXAMPLE 2

The separation of verapamil was conducted by the use of the separatory column for optical isomers prepared in Example 2.

Conditions of high-performance liquid chromatography mobile phase: 50 mM phosphate buffer (pH 4.5) containing 5% of ethanol flow rate: 1.0 ml/min detection: 230 nm The result is shown in FIG. 4.

The enantiomers are eluted at a retention time of 2.5 minutes for the d-isomer, and a retention time of 3.5 minutes for the l-isomer. As is apparent from FIG. 4, the optical isomers of verapamil can be separated by the use of the separating agent of the present invention.

Figure 1:
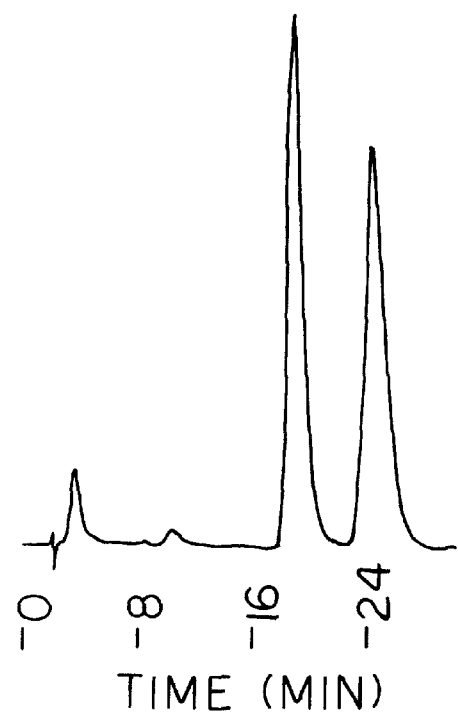
FIG. 1 shows the liquid chromatogram of d,l-azelastine obtained by using the column according to the present invention.
Figure 2:
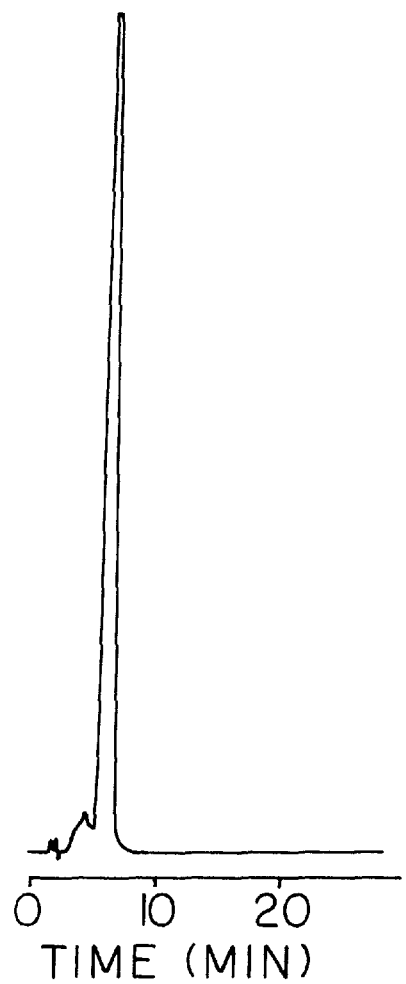
FIGS. 2 and 3 show the liquid chromatograms of d,l-azelastine obtained by using an ovomucoid column.
Figure 3:
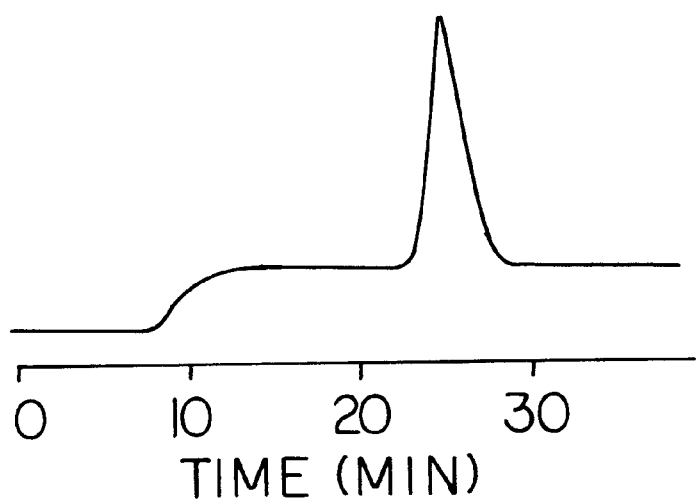
Figure 4:
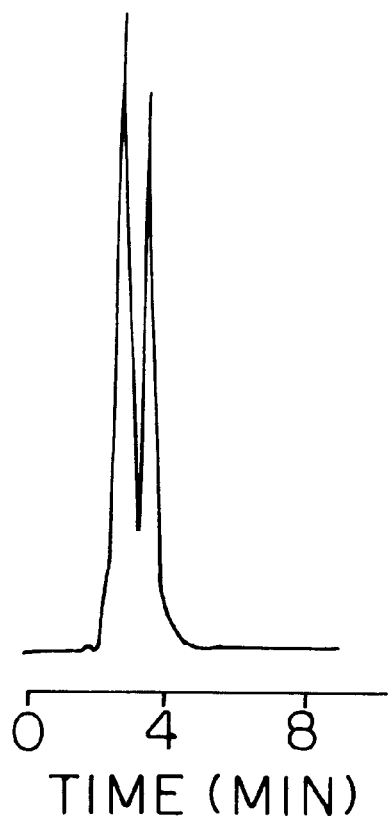
FIG. 4 shows the liquid chromatogram of d,l-verapamil obtained by using the column according to the present invention.

In the FIGS. 1 and 4, each left peak is assignable to d-isomer, while each right peak to l-isomer thereby exhibiting the distinct separation of each enantiomer.

We claim:

1. An optical isomer separating agent characterized by being composed of a stationary phase comprising a support and a conalbumin which is partially chemically converted by cross-linkage with glutaraldehyde, conversion into a diol, acylation or modification with glutaraldehyde followed by reduction.

* * * * *